United States Patent [19]

Willms

[11] Patent Number: 5,051,525

[45] Date of Patent: Sep. 24, 1991

[54] N-ACYL-2-AMINO ACID AMIDES CONTAINING PHOSPHINIC ESTERS, PROCESS FOR THEIR PREPARATION, AND N-ACYL-2-AMINO ACIDS NITRILES AS PRECURSORS

[75] Inventor: Lothar Willms, Hillscheid, Fed. Rep. of Germany

[73] Assignee: Hoechst Aktiengesellschaft, Frankfurt am Main, Fed. Rep. of Germany

[21] Appl. No.: 474,148

[22] Filed: Feb. 2, 1990

[30] Foreign Application Priority Data

Feb. 6, 1989 [DE] Fed. Rep. of Germany ....... 3903446
May 20, 1989 [DE] Fed. Rep. of Germany ....... 3916551

[51] Int. Cl.$^5$ .................. C07F 9/02; C07C 231/00
[52] U.S. Cl. ................... 558/145; 558/166; 558/191; 564/129; 564/159; 564/197
[58] Field of Search ............... 558/76, 77, 78, 8, 145, 558/166, 191; 564/129, 159, 197

[56] References Cited

U.S. PATENT DOCUMENTS

| | | | |
|---|---|---|---|
| 4,168,963 | 9/1979 | Rupp et al. | 71/86 |
| 4,521,348 | 6/1985 | Finke et al. | |
| 4,692,541 | 9/1987 | Zeiss et al. | 558/5 |

FOREIGN PATENT DOCUMENTS

| | | | |
|---|---|---|---|
| 0011245 | 5/1980 | European Pat. Off. | |
| 2717440 | 12/1977 | Fed. Rep. of Germany | 71/86 |
| 1587292 | 4/1981 | United Kingdom | 71/86 |

OTHER PUBLICATIONS

Natchev, Bulletin of the Chemical Society of Japan, vol. 61 (10), 1988, pp. 3699-3704.

Becke et al., Liebigs Annalen der Chemie, 713, 212-214 (1968).
Becke et al., Liebigs Annalen der Chemie, 749, 198-201 (1971).
Jones, J. Chem. Soc. (C), 1230-1232 (1970).

*Primary Examiner*—José G. Dees
*Assistant Examiner*—D. D. Carr
*Attorney, Agent, or Firm*—Curtis, Morris & Safford

[57] ABSTRACT

N-acyl-2-amino acid amides containing phosphinic esters, process for their preparation, and N-acyl-2-amino acid nitriles as precursors Phosphorus-containing N-acyl-2-amino acid amides of the general formula (I)

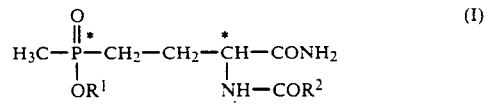

where
R$^1$ is alkyl, optionally substituted by halogen or alkoxy, or is benzyl or phenyl, each of which is optionally substituted by alkyl, alkoxy, halogen, nitro or CF$_3$, or is cycloalkyl, and
R$^2$ is H, or alkyl, optionally substituted by halogen or alkoxy, or is (CH$_2$)$_n$-phenyl, optionally substituted in the phenyl ring by alkyl, alkoxy, halogen, nitro or CF$_3$, where n=0, 1, 2 or 3, are valuable intermediates for the preparation of L-phosphinothricin by enzymatic cleavage, and can be obtained from the corresponding N-acyl-2-amino acid nitrile by selective acid hydrolysis.

11 Claims, No Drawings

N-ACYL-2-AMINO ACID AMIDES CONTAINING PHOSPHINIC ESTERS, PROCESS FOR THEIR PREPARATION, AND N-ACYL-2-AMINO ACIDS NITRILES AS PRECURSORS

Description

N-Acyl-2-amino acid amides containing phosphinic esters, process for their preparation, and N-acyl-2-amino acid nitriles as precursors.

The present invention relates to phosphorus-containing N-acyl-2-amino acid amides of the general formula (I)

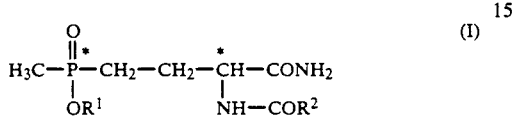

where
R$^1$ is C$_1$–C$_{14}$-alkyl which is branched or unbranched and unsubstituted or monosubstituted or polysubstituted by halogen or C$_1$–C$_6$-alkoxy, or is benzyl or phenyl, benzyl or phenyl being unsubstituted or monosubstituted or polysubstituted in the phenyl ring by C$_1$–C$_4$-alkyl, C$_1$–C$_4$-alkoxy, halogen, nitro or trifluoromethyl, or is C$_3$–C$_{10}$-cycloalkyl, and
R$^2$ is hydrogen, C$_1$–C$_{14}$-alkyl which is unsubstituted or monosubstituted or polysubstituted by halogen or C$_1$–C$_4$-alkoxy, or is a radical of the formula —(CH$_2$)$_n$-phenyl which is unsubstituted or monosubstituted to trisubstituted in the phenyl ring by C$_1$–C$_4$-alkyl, C$_1$–C$_4$-alkoxy, halogen, nitro or trifluoromethyl and in which n is 0, 1, 2 or 3.

Compounds of the formula (I) which are of particular interest are those where
R$^1$ is unbranched or branched C$_1$–C$_{10}$-alkyl or C$_1$–C$_{10}$-alkyl which is monosubstituted to trisubstituted by halogen, such as fluorine or chlorine, or is C$_5$–C$_6$-cycloalkyl, and
R$^2$ is hydrogen, unbranched or branched C$_1$–C$_{14}$-alkyl which is unsubstituted or substituted by one to three radicals from the group comprising halogen and C$_1$–C$_4$-alkoxy, or is a radical of the formula —(CH$_2$)$_n$-phenyl, the phenyl ring being unsubstituted or monosubstituted to trisubstituted by halogen and n being 0, 1 or 2.

Preferred compounds of the formula (I) are those where
R$^1$ is unbranched C$_1$–C$_8$-alkyl or cyclohexyl, and
R$^2$ is C$_1$–C$_4$-alkyl or benzyl.

Examples of suitable meanings of R$^1$ are the radicals methyl, ethyl, n-propyl, i-propyl, n-, i-, t- and 2-butyl, n-, i-, t-, 2-, 3- and neo-pentyl, n-, i- and 2-hexyl, heptyl, octyl, nonyl, decyl, undecyl, dodecyl, tridecyl, tetradecyl, 2-chloroethyl, 2,2-dichloroethyl, 1,1,2,2-tetrafluoroethyl, 2-methoxyethyl, 1-ethoxyethyl, 2,2-dimethoxyethyl, 3-methoxypropyl, benzyl, phenyl, o- and p-tolyl, 2-methoxyphenyl, 4-nitrophenyl, 2- or 3-chlorophenyl, 4-trifluoromethylphenyl, 4-chlorobenzyl, cyclopropyl, cyclobutyl, cyclopentyl, cyclohexyl, 4,4-dimethylcyclohexyl, cycloheptyl and cyclooctyl.

Examples of suitable meanings of R$^2$ are hydrogen, radicals as listed in the case of R$^1$, 1- and 2-phenylethyl, 1-phenylpropyl, 3-phenylpropyl and 1-(2-chlorophenyl)ethyl. Halogen in each case is fluorine, chlorine and/or bromine, preferably fluorine and/or chlorine.

The invention also relates to a process for the preparation of the compounds of the formula (I) according to the invention, which comprises subjecting N-acyl-2-amino acid nitriles of the formula (II)

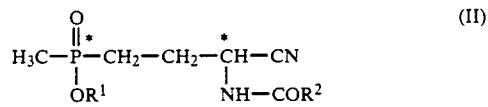

where
R$^1$ and R$^2$ have the meanings indicated in the case of formula (I), to selective acid hydrolysis on the nitrile group to give the corresponding carboxamide of the general formula (I).

In the compounds of the formulae (I) and (II), there are two centers of chirality, so that either the mixtures of diastereomers or enantiomers or individual diastereomers or enantiomers of the formula (II) can be employed in the process according to the invention. The hydrolysis on the nitrile group proceeds virtually while maintaining the configuration on the two centers of chirality which have been mentioned. If, for example, an α-D-isomer of the formula (II) is employed which is optically pure with regard to the center of chirality in the α-position relative to the nitrile group and which is only present as a mixture of stereoisomers with regard to the center of chirality on the phosphinic ester group, hydrolysis of the nitrile function according to the invention gives the α-D-N-acyl-amino acid amide of the general formula (I) while maintaining the configuration (optical activity) with regard to the α-position relative to the nitrile group.

The invention also relates to compounds of the formula (II) which can be used as intermediates for the preparation of the compounds of the formula (I) according to the invention and in which R$^1$ and R$^2$ have the meanings mentioned in the case of formula (I). In formula (II), R$^1$ and R$^2$ preferably have the meanings preferred in the case of formula (I).

The starting materials of the formula (II) which are required for preparing the compounds of the general formula (I) according to the invention may be prepared, for example, by acylation of α-amino acid nitriles of the general formula (III)

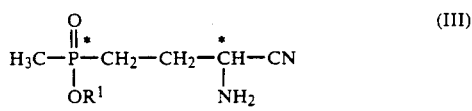

with acid chlorides of the formula R$^2$-COCl, or acid anhydrides of the formula (R$^2$CO)$_2$O, by processes which are generally customary (cf. Organikum [Laboratory Practice of Organic Chemistry], VEB Deutscher Verlag der Wissenschaften, Berlin 1976, 512 et seq.). The amino acid nitriles of the formula (III) are known from EP-A 194,521 (U.S. Pat. No. 4,692,541) and EP-A 011,245 (U.S. Pat. No. 4,521,348), or they can be prepared for example by the processes known from these references.

The process according to the invention is carried out in such a way that compounds of the formula (II) are selectively hydrolyzed on the nitrile function under suitable reaction conditions to give the corresponding carboxamide of the formula (I), during which process the N-acyl group, or phosphinic ester group, are not attracted or hydrolyzed, or only to a negligible extent. The process is carried out for example in formic acid, if appropriate in the presence of Lewis acids, such as hydrogen halides, for example hydrogen chloride or hydrogen bromide, if appropriate in the presence of an inert organic solvent, such as, for example, dichloromethane, toluene or chlorobenzene. Analogous reaction conditions are known from Liebigs Annalen der Chemie 713, 212 (1968); loc. sit. 749, 198 (1971); J. Chem. Soc. [C], 1970, 1230. Formic acid can be employed in 100% pure form or in a lower concentration, i.e., diluted with water. Formic acid is employed in amounts of 90 to 600 mol-%, preferably in equimolar amounts or a 2- to 3-fold excess, based on the compound of the formula (II).

The process according to the invention is preferably carried out at reaction temperatures of 0°–260° C., in particular at below 250° C., and under pressure using formic acid without Lewis catalysts, or at 0°–60° C. using formic acid in the presence of Lewis catalysts. The Lewis acids are generally employed in catalytic amounts, for example 0.1 to 2 mol-%, preferably about 0.5 mol-%, or, alternatively, in excess, for example 150 to 600 mol-%.

Depending on the reaction conditions, the duration of the reaction can vary within wide limits, but it is generally 0.1 to 48 hours, preferably 0.5 to 6 hours.

The preparation process according to the invention for compounds of the formula (I) is surprisingly selective. The N-acyl-2-amino acid nitriles of the general formula (II) are selectively cleaved to give the N-acyl-amino acid amides of the general formula (I), in which process for example the acid-labile phosphinic ester group or the N-acyl group, which can likewise be cleaved under acid conditions, are attacked to a negligible extent only. DE-A 2,717,440 (GB-A-1,587,292) or EP-A 011,245 disclose processes according to which for example ethyl 3-amino-3-cyano-propyl(methyl)-phosphinate, prepared in a Strecker synthesis, is cleaved completely using hydrochloric acid to give the corresponding 3-amino-3-carboxy-propyl(methyl)phosphinic acid. From Liebigs Ann. Chem. 749, 198 (1971) it is known that dimethyl (2-cyanoethyl)phosphonate is cleaved in formic acid/hydrogen chloride to give (2-amidocarbonylethyl)phosphonic acid, during which process partial hydrolysis to give monomethyl or dimethyl (2-amidocarbonylethyl)phosphonate obviously does not take place. Compared with this process, the process according to the invention permits carboxamides containing phosphinic esters, of the general formula (I), to be prepared in almost quantitative yields, i.e., virtually without hydrolysis on the phosphinic ester group.

The N-acyl-α-amino acid amides of the general formula (I) are valuable precursors which can be cleaved enzymatically to give L-phosphinothricin with high excesses of enantiomers (cf. German Patent Application P 3903446.1, HOE 89/F 042). L-Phosphinothricin has bactericidal (Helv. Chim. Acta. 55, 224 (1972)), fungicidal (Sci. Rep. Meiji Seika Kaisha 13, 34 (1973)) and excellent herbicidal properties (DE-A 2,717,440, EP-A 54,897).

The examples below are intended to illustrate the invention in greater detail without restricting it to the concrete examples.

EXAMPLE 1

Cyclohexyl D,L-(3-phenylacetamido-3-aminocarbonylpropyl)methylphosphinate (a) Cyclohexyl D,L-(3-acetoxy-3-cyanopropyl)methylphosphinate (preparation analogously to EP-11,245); 50 g (0.4 mol) of acroleincyanohydrin acetate which contains 4 g of t-butyl peroctoate are added dropwise within 1 hour at 120° C. under a nitrogen atmosphere to 130 g (0.8 mol) of monocyclohexyl methanephosphonite. When the dropwise addition is complete, stirring is continued at 120° C. for 15 minutes, and the mixture is subsequently subjected to fractional distillation under reduced pressure. This gives 106 g (92% of theory) of cyclohexyl D,L-(3-acetoxy-3-cyanopropyl)methylphosphinate of boiling point 178° to 180° C. at 0.02 mbar.

(b) Cyclohexyl D,L-(3-phenylacetamido-3-cyanopropyl)methylphosphinate; 28.7 g (0.1 mol) of cyclohexyl D,L-(3-acetoxy-3cyanopropyl)methylphosphinate are added dropwise at 20° C. within 1 hour to 29.6 ml of concentrated ammonia. The reaction mixture is subsequently extracted using methylene chloride, and the extract is dried over sodium sulfate and treated with 10.2 g (0.1 mol) of triethylamine. 15.4 g (0.1 mol) of phenylacetyl chloride are added dropwise at 0° C. After the mixture has been stirred for 18 hours at room temperature, it is treated with 50 ml of water, a pH of 5 is established using 0.5 N hydrochloric acid, and the mixture is extracted using methylene chloride. The oil which remains after the methylene chloride extract has been evaporated off is purified by chromatography on silica gel (mobile phase: methylene chloride). This gives 27.5 g (76% of theory) of cyclohexyl D,L-(3-acetoxy-3-cyanopropyl)methylphosphinate; $^1$H-NMR (CDCl$_3$): $\delta = 9.45$ (NH, m, 1H); 7.3 (C$_6$H$_5$, s, 5H); 4.95 (CH, m, 1H); 4.36 (CH, m, 1H); 3.6 (CH$_2$, s, 2H); 1.2–2.2 (CH$_2$CH$_2$, PCH$_3$, C$_6$H$_{10}$, m, 17H).

(c) Cyclohexyl D,L-(3-phenylacetamido-3-aminocarbonylpropyl)methylphosphinate; 6 g (0.01 mol) of cyclohexyl D,L-(3-phenylacetamido-3-cyanopropyl)methylphosphinate are dissolved in 40 ml of formic acid. After this, HCl gas is passed in at room temperature. After 3 hours, the reaction mixture is concentrated, the residue is dissolved in methylene chloride and water, and the pH of 5 is established using sodium hydrogen carbonate. After the mixture has been extracted using methylene chloride, the methylene chloride extracts are dried over sodium sulfate and subjected to evaporation on a rotary evaporator. The crude product which remains is purified by chromatography on silica gel (mobile phase: methylene chloride/methanol 9:1). This gives 5.90 g (94.1% of theory) of a pale yellow oil; $^1$H-NMR (CDCl$_3$): $\delta = 7.2$ (C$_6$H$_5$, s, 5H); 7.2 (CONH$_2$, d, 2H); 5.6 (NH, s, 1H); 4.2–4.8 (2×CH, m, 2H); 3.6 (Ch$_2$, s, 2H); 1.2–2.3 (CH$_2$CH$_2$, PCH$_3$, C$_6$H$_{10}$, m, 17H).

After some weeks, the substance crystallizes to give a finely-crystalline, colorless powder of a melting point 128° to 130° C.

Examples 2(b) to 50(b)

The compounds of the general formula (II) which are mentioned in Table 1 below may be prepared analogously to the N-acyl-α-amino acid nitrile described in Example 1(b).

TABLE 1

$$\begin{array}{c}CH_3\;\;O\\\diagdown\;\;\|\\P-CH_2CH_2-CH-CN\\\diagup\;\;\;\;\;\;\;\;\;\;\;\;\;\;\;\;\;\;\;\;\;|\\R^1O\;\;\;\;\;\;\;\;\;\;\;\;\;\;\;\;\;\;\;\;\;\;NH-COR^2\end{array}\qquad(II)$$

| Ex. No. | $R^1$ | $R^2$ | mp | $n_D^{20}$ |
|---|---|---|---|---|
| 2b | $CH_3$ | $CH_3$ | resin | |
| 3b | $C_2H_5$ | $CH_3$ | | |
| 4b | n-$C_3H_7$ | $CH_3$ | | |
| 5b | i-$C_3H_7$ | $CH_3$ | | 1.4600 |
| 6b | n-$C_4H_9$ | $CH_3$ | | |
| 7b | i-$C_4H_9$ | $CH_3$ | 40–42° C. | |
| 8b | sec.-$C_4H_9$ | $CH_3$ | | |
| 9b | n-$C_5H_{11}$ | $CH_3$ | | |
| 10b | i-$C_5H_{11}$ | $CH_3$ | | |
| 11b | n-$C_6H_{13}$ | $CH_3$ | | |
| 12b | Cyclopentyl | $CH_3$ | | 1.4280 |
| 13b | Cyclohexyl | $CH_3$ | | |
| 14b | n-$C_7H_{15}$ | $CH_3$ | | |
| 15b | n-$C_8H_{17}$ | $CH_3$ | | |
| 16b | $ClC_2H_4$ | $CH_3$ | | |
| 17b | $CH_3$ | Benzyl | resin | |
| 18b | $C_2H_5$ | " | | |
| 19b | n-$C_3H_7$ | " | | |
| 20b | i-$C_3H_7$ | " | resin | |
| 21b | n-$C_4H_9$ | " | | |
| 22b | i-$C_4H_9$ | " | resin | |
| 23b | sec.-$C_4H_9$ | " | | |
| 24b | n-$C_5H_{11}$ | " | | |
| 25b | i-$C_5H_{11}$ | " | | |
| 26b | n-$C_6H_{13}$ | " | | |
| 27b | Cyclopentyl | " | | |
| 28b | $CH_3$ | $C_2H_5$ | | |
| 29b | $C_2H_5$ | " | | |
| 30b | n-$C_3H_7$ | " | | |
| 31b | i-$C_4H_9$ | " | | |
| 32b | Cyclohexyl | " | | |
| 33b | Cyclopentyl | " | | |
| 34b | Cl—$CH_2CH_2$ | $C_2H_5$ | | |
| 35b | $CH_3OCH_2CH_2$ | $CH_3$ | | |
| 36b | $C_6H_5$ | $CH_3$ | | |
| 37b | $CH_2C_6H_5$ | $CH_3$ | | |
| 38b | 4-$NO_2$—$C_6H_4$ | $CH_3$ | | |
| 39b | 2-$ClC_6H_4$ | $CH_3$ | | |
| 40b | Cyclohexyl | $CH_2CH_2C_6H_5$ | | |
| 41b | $CH_3$ | " | | |
| 42b | i-$C_3H_7$ | " | | |
| 43b | $CH_3$ | $C_6H_5$ | | |
| 44b | Cyclohexyl | " | | |
| 45b | $CH_3$ | 2-Cl—$C_6H_4$ | | |
| 46b | $CH_3$ | p-Tolyl | | |
| 47b | $CH_3$ | 2,4-$Cl_2$—$C_6H_4$ | | |
| 48b | $CH_3$ | 3-$OCH_3$—$C_6H_4$ | | |
| 49b | $CH_3$ | 4-$CH_2$—$C_6H_4$—$CH_2$ | | |
| 50b | $CH_3$ | 2-Cl—$C_6H_4$—$CH_2$ | | |

Examples 2(c) to 50(c)

For example, the compounds of the general formula (I) listed in Table 2 may be prepared analogously to the N-acyl-α-amino acid amide described in Example 1(c).

TABLE 2

$$\begin{array}{c}CH_3\;\;O\\\diagdown\;\;\|\\P-CH_2CH_2-CH-CONH_2\\\diagup\;\;\;\;\;\;\;\;\;\;\;\;\;\;\;\;\;\;\;\;\;|\\R^1O\;\;\;\;\;\;\;\;\;\;\;\;\;\;\;\;\;\;\;\;\;\;NH-CO-R^2\end{array}\qquad(I)$$

| Ex. No. | $R^1$ | $R^2$ | mp | $n_D^{20}$ |
|---|---|---|---|---|
| 2c | $CH_3$ | $CH_3$ | resin | |
| 3c | $C_2H_5$ | $CH_3$ | | |
| 4c | n-$C_3H_7$ | $CH_3$ | | |
| 5c | i-$C_3H_7$ | $CH_3$ | | 1.4622 |
| 6c | n-$C_4H_9$ | $CH_3$ | | |
| 7c | i-$C_4H_9$ | $CH_3$ | 126–170 | |
| 8c | sec.-$C_4H_9$ | $CH_3$ | | |
| 9c | n-$C_5H_9$ | $CH_3$ | | |
| 10c | i-$C_5H_9$ | $CH_3$ | | |
| 11c | n-$C_6H_{11}$ | $CH_3$ | | |
| 12c | Cyclopentyl | $CH_3$ | 164–165 | |
| 13c | Cyclohexyl | $CH_3$ | 85–86 | |
| 14c | n-$C_7H_{15}$ | $CH_3$ | | |
| 15c | n-$C_8H_{17}$ | $CH_3$ | | |
| 16c | $ClC_2H_4$ | $CH_3$ | 44–45 | |
| 17c | $CH_3$ | Benzyl | | |
| 18c | $C_2H_5$ | " | resin | |
| 19c | n-$C_3H_7$ | " | | |
| 20c | i-$C_3H_7$ | " | | |
| 21c | n-$C_4H_9$ | " | | |
| 22c | i-$C_4H_9$ | " | | |
| 23c | sec.-$C_4H_9$ | " | | |
| 24c | n-$C_5H_{11}$ | " | | |
| 25c | i-$C_5H_{11}$ | " | | |
| 26c | n-$C_6H_{13}$ | " | | |
| 27c | Cyclopentyl | " | | |
| 28c | $CH_3$ | $C_2H_5$ | | |
| 29c | $C_2H_5$ | " | | |
| 30c | n-$C_3H_7$ | " | | |
| 31c | i-$C_4H_9$ | " | | |
| 32c | Cyclohexyl | " | | |
| 33c | Cyclopentyl | " | | |
| 34c | Cl—$CH_2CH_2$ | $C_2H_5$ | | |
| 35c | $CH_3OCH_2CH_2$ | $CH_3$ | | |
| 36c | $C_6H_5$ | $CH_3$ | | |
| 37c | $CH_2C_6H_5$ | $CH_3$ | | |
| 38c | 4-$NO_2$—$C_6H_4$ | $CH_3$ | | |
| 39c | 2-$ClC_6H_4$ | $CH_3$ | | |
| 40c | Cyclohexyl | $CH_2CH_2C_6H_5$ | | |
| 41c | $CH_3$ | " | | |
| 42c | i-$C_3H_7$ | " | | |
| 43c | $CH_3$ | $C_6H_5$ | | |
| 44c | Cyclohexyl | " | | |
| 45c | $CH_3$ | 2-Cl—$C_6H_4$ | | |
| 46c | $CH_3$ | p-Tolyl | | |
| 47c | $CH_3$ | 2,4-$Cl_2$—$C_6H_4$ | | |
| 48c | $CH_3$ | 3-$OCH_3$—$C_6H_4$ | | |
| 49c | $CH_3$ | 4-$CH_2$—$C_6H_4$—$CH_2$ | | |
| 50c | $CH_3$ | 2-Cl—$C_6H_4$—$CH_2$ | | |

I claim:
1. An N-acyl-2-amino acid amide of the formula (I)

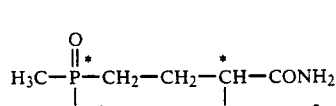

where $R^1$ is $C_1$–$C_{14}$-alkyl which is branched or unbranched and unsubstituted or monosubstituted or polysubstituted by halogen or $C_1$–$C_6$-alkoxy, or is benzyl or phenyl, benzyl or phenyl being unsubstituted or monosubstituted or polysubstituted in the phenyl. ring by $C_1$–$C_4$-alkyl, $C_1$–$C_4$-alkoxy, halogen, nitro or trifluoromethyl, or is $C_3$–$C_{10}$-cycloalkyl, and $R^2$ is hydrogen, $C_1$–$C_{14}$-alkyl which is unsubstituted or monosubstituted or polysubstituted by halogen or $C_1$–$C_4$-alkoxy, or is a radical of the formula —$(CH_2)_n$-phenyl which is unsubstituted or monosubstituted to trisubstituted in the phenyl ring by $C_1$–$C_4$-alkyl, $C_1$–$C_4$-alkoxy, halogen, nitro or trifluoromethyl and in which n is 0, 1, 2 or 3, with the proviso that $R^1$ is not ethyl when $R^2$ is methyl.

2. A compound of the formula (I) as claimed in claim 1, wherein $R^1$ is unbranched or branched $C_1$–$C_{10}$-alkyl or $C_1$–$C_{10}$-alkyl which is monosubstituted to trisubstituted by halogen, or is $C_5$–$C_6$-cycloalkyl, and $R^2$ is hydrogen, unbranched or branched $C_1$–$C_{14}$-alkyl which is unsubstituted or substituted by one to three radicals from the group comprising halogen and $C_1$–$C_4$-alkoxy, or is a radical of the formula —$(CH_2)_n$—phenyl, the phenyl ring being unsubstituted or monosubstituted to trisubstituted by halogen and n being 0, 1 or 2.

3. A compound of the formula (I) as claimed in claim 1, wherein $R^1$ is unbranched $C_1$–$C_8$-alkyl or cyclohexyl, and
$R^2$ is $C_1$–$C_4$-alkyl or benzyl.

4. A compound of the formula (II)

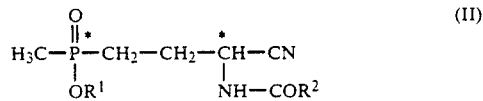

wherein $R^1$ is $C_1$–$C_{14}$-alkyl which is branched or unbranched and unsubstituted or monosubstituted or polysubstituted by halogen or $C_1$–$C_6$-alkoxy, or is benzyl or phenyl, benzyl or phenyl being unsubstituted or monosubstituted or polysubstituted in the phenyl ring by $C_1$–$C_4$-alkyl, $C_1$–$C_4$-alkoxy, halogen, nitro or trifluoromethyl, or is $C_3$–$C_{10}$-cycloalkyl, and $R^2$ is a radical of the formula —$(CH_2)_n$-phenyl which is unsubstituted or monosubstituted to trisubstituted in the phenyl ring by $C_1$–$C_4$-alkyl, $C_1$–$C_4$-alkoxy, halogen, nitro or trifluoromethyl and in which n is 0, 1, 2 or 3.

5. A compound of the formula II as claimed in claim 4, where $R^1$ is unbranched or branched $C_1$–$C_{10}$-alkyl or $C_1$–$C_{10}$-alkyl which is monosubstituted to trisubstituted by halogen, or is $C_5$–$C_6$-cycloalkyl, and $R^2$ is a radical of the formula —$(CH_2)_n$-phenyl, the phenyl ring being unsubstituted or monosubstituted to trisubstituted by halogen and n being 0, 1 or 2.

6. A compound as claimed in claim 4, wherein $R^1$ is unbranched $C_1$–$C_8$-alkyl or cyclohexyl, and
$R^2$ is benzyl.

7. A process for the preparation of a compound of the formula (I)

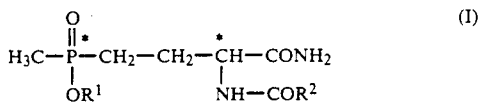

where $R^1$ is $C_1$–$C_{14}$-alkyl which is branched or unbranched and unsubstituted or monosubstituted or polysubstituted by halogen or $C_1$–$C_6$-alkoxy, or is benzyl or phenyl, benzyl or phenyl being unsubstituted or monosubstituted or polysubstituted in the phenyl ring by $C_1$–$C_4$-alkyl, $C_1$–$C_4$-alkoxy, halogen, nitro or trifluoromethyl, or is $C_3$–$C_{10}$-cycloalkyl, and $R^2$ is hydrogen, $C_1$–$C_{14}$-alkyl which is unsubstituted or monosubstituted or polysubstituted by halogen or $C_1$–$C_4$-alkoxy, or is a radical of the formula —$(CH_2)_n$-phenyl which is unsubstituted or monosubstituted to trisubstituted in the phenyl ring by $C_1$–$C_4$-alkyl, $C_1$–$C_4$-alkoxy, halogen, nitro or trifluoromethyl and in which n is 0, 1, 2 or 3, which comprises subjecting an N-acyl-2-amiano acid nitrile of the formula (II)

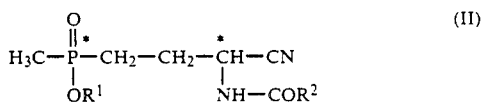

where $R^1$ and $R^2$ have the meanings indicated in the case of formula (I), to selective acid hydrolysis on the nitrile group, to give the corresponding carboxamide of the formula (I).

8. The process as claimed in claim 7, in which the hydrolysis is carried out in formic acid or aqueous formic acid.

9. The process as claimed in claim 7, in which the hydrolysis is carried out using formic acid in the presence of hydrogen halide.

10. The process as claimed in claim 7, in which a solvent is used which is inert under the reaction conditions.

11. The process as claimed in claim 7, in which the hydrolysis is carried out at 0° to 250° C.

* * * * *